United States Patent [19]

Kodama et al.

[11] Patent Number: 5,028,597

[45] Date of Patent: Jul. 2, 1991

[54] ANTITHROMBOGENIC MATERIALS

[75] Inventors: Makoto Kodama; Tsukasa Sakai; Keishiro Tsuda, all of Ibaraki; Koichi Okita; Shigeru Asako, both of Osaka; Masaharu Komamiya, Saitama; Hiroshi Oinuma, Saitama, all of Japan

[73] Assignees: Agency of Industrial Science and Technology, Tokyo; Sumitomo Electric Industries, Ltd., Osaka; Watanabe Pharmaceutical Industry Co., Ltd., Saitama, all of Japan

[21] Appl. No.: 515,768

[22] Filed: Apr. 13, 1990

Related U.S. Application Data

[63] Continuation of Ser. No. 35,338, Apr. 7, 1987, abandoned.

[30] Foreign Application Priority Data

Apr. 7, 1986 [JP] Japan .................................. 61-78098
Mar. 27, 1987 [JP] Japan .................................. 62-73157

[51] Int. Cl.$^5$ .................. A61K 37/12; A61K 31/725; A61F 2/04
[52] U.S. Cl. ........................................ 514/56; 514/54; 623/1; 623/11; 623/12; 128/DIG. 8
[58] Field of Search ................. 514/54, 56, 21; 623/1, 623/11, 12; 128/DIG. 8

[56] References Cited

U.S. PATENT DOCUMENTS

| | | | |
|---|---|---|---|
| 4,350,629 | 9/1982 | Yannas et al. | 260/123.7 |
| 4,448,718 | 5/1984 | Yannas et al. | 128/DIG. 8 |
| 4,678,468 | 7/1987 | Hiroyoshi | 623/1 |

FOREIGN PATENT DOCUMENTS

| | | | |
|---|---|---|---|
| 0212881 | 3/1987 | European Pat. Off. | |
| 0230635 | 8/1987 | European Pat. Off. | |
| 0190966 | 9/1985 | Japan | 623/1 |
| 2033232 | 5/1980 | United Kingdom | |

OTHER PUBLICATIONS

European Search Report.

Primary Examiner—David M. Naff
Assistant Examiner—Jean C. Witz
Attorney, Agent, or Firm—Sughrue, Mion, Zinn, Macpeak & Seas

[57] ABSTRACT

An antithrombogenic material is described, comprising an expanded polytetrafluoroethylene base having a collagen layer provided on the surface thereof, and further provided thereon a composite layer of collagen and a mucopolysaccharide, and said collagen is crosslinked with a crosslinking agent.

4 Claims, 1 Drawing Sheet

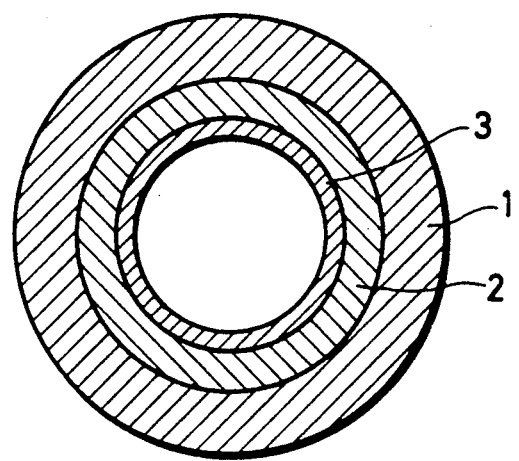

ANTITHROMBOGENIC MATERIALS

This is a continuation of application Ser. No. 07/035,338 filed Apr. 7, 1987, now abandoned.

FIELD OF THE INVENTION

The present invention relates to a novel antithrombogenic material, and more particularly, to an expanded polytetrafluoroethylene material for clinical application having an excellent antithrombogenic property and compatibility with a living body which are suited for use in e.g., artificial blood vessels and blood vessel catheters.

BACKGROUND OF THE INVENTION

In recent years, a variety of medical equipment, for example, artificial blood vessels, blood vessel catheters, tubes for artificial kidney, artificial hearts and lung, blood bypath tubes, etc., have become widely used in various manners in which they are brought into direct contact with blood.

These medical equipments used at regions which are brought into direct contact with blood are required to have not only a good elasticity, durability, wet strength, etc., but also are required to be excellent particularly in an antithrombogenic property and compatibility with a living body.

Accordingly, polymers such as nylons, polyesters, polyethylene, polypropylene, polyurethane, fluorine resins, etc. to which an antithrombogenic property and a compatibility with a living body have been imparted are used as materials of such medical equipment.

As a method for imparting an antithrombogenic property to the polymers described above, there have been hitherto known in the art a method in which the materials per se are modified to be those resistant to thrombus formation, a method which comprises incorporating or binding with chemical bonds a natural anticoagulant such as heparin to the materials, a method which comprises coating, e.g., collagen having excellent compatibility with a living body on the surface of the materials, and the like.

Among the methods noted above, examples of the method in which a material per se is modified to be resistant to thrombus formation include a certain polyurethane compound having such a structure that hydrophobic and hydrophilic portions appear on the surface thereof alternately (as described in U.S. Pat. Nos. 4,242,474 and 4,465,480); and a base polymer having bound thereto a hydrogel or a hydrophilic polymer (as described in Japanese Patent Application (OPI) No. 22926/85) (the term "OPI" used herein means published unexamined patent application). However, these polymers are still not totally satisfactory for practical use, although these materials do show a considerably high antithrombogenic property, and thus fully satisfactory materials have not yet been obtained.

Examples of the method for chemically binding a natural anticoagulant such as heparin to the material include a method which comprises graft polymerizing a vinyl compound having a tertiary amino group to a base polymer, quaternizing the amino group in the grafted polymer, and then heparinizing the same (as described in Japanese Patent Applicaiton (OPI) Nos. 206753/83 and 31868/82). However, the thus heparinized polymer is defective in that desired dynamic strength inherent to the base polymer is reduced, and strength and durability necessary for practical use cannot be obtained.

Furthermore, examples of the method which comprises, e.g., coating collagen onto the surface of the material include a method which comprises subjecting the surface of polyethylene, polypropylene, polyester, etc. to a polarization treatment, e.g., a treatment with chromic acid or an alkali, to render the surface hydrophilic, coating collagen onto the surface, and irradiating to effect binding of the coated collagen (as described in Japanese Patent Publication No. 37433/71), and a method which comprises subjecting the surface of a silicone rubber material to a polarization treatment such as plasma glow discharge treatment, a chemical treatment, etc., to render the surface hydrophilic, and then coating collagen in a manner as described above (as described in Japanese Patent Publication No. 4559/74). However, even the thus collagen-coated polymers provide only an insufficient antithrombogenic property and are not necessarily satisfactory for clinical applicaiton.

On the other hand, those using living materials themselves such as collagen (e.g., a tube made of collagen per se as described in European Patent Application 83302178A and 83302077A, and a porous substrate having provided thereon collagen as described in British Patents 2,153,235 and 2,153,685) have excellent compatibility with a living body as compared to the aforesaid polymers, but still encounter a problem with respect to antithrombogenic property.

As such, materials suited for clinical application which are sufficiently satisfactory with respect to both an antithrombogenic property and compatibility with a living body have not been yet found heretofore; particularly with respect to artificial blood vessels having an inner diameter of from 1 to 3 mm, it is the actual situation that materials which can fully prevent thrombus formation suddenly caused after transplantation have not yet been developed.

The present inventors have made extensive investigations to obtain materials suitable for clinical application having an excellent antithrombogenic property and compatibility with a living body, and previously developed polymers having bound mucopolysaccharides to the surface thereof activated by a plasma glow discharge treatment (as described in Japanese Patent Application (OPI) No. 183762/84), polymers having provided a collagen layer on the surface thereof and further provided thereon a heparin layer via a layer of fibronectin known as a cell adhesive protein (as described in Japanese Patent Application (OPI) No. 190966/85), and polymers having laminated thereon a layer of a mixture of an antithrombogenic mucopolysaccharides and collagen from which antigenic groups have been removed, or a gelatinized product thereof on the surface of the materials followed by crosslinking with a polyvalent aldehyde compound (as described in Japanese Patent Application (OPI) No. 191364/86).

However, these antithrombogenic materials are still insufficient to fully satisfy both the desired antithrombogenic property and compatibility with a living body at the same time, although they are improved to a considerable degree as compared to earlier materials. Thus, further improved materials are necessary.

SUMMARY OF THE INVENTION

An object of the present invention is to provide materials excellent both in an antithrombogenic property and compatibility with a living body which are suited for artificial blood vessels, and good in durability suited for clinical application.

The above and other objects of the present invention are attained by an antithrombogenic material comprising an expanded polytetrafluoroethylene base having a collagen layer provided on the surface thereof, and further provided thereon a composite layer of collagen and mucopolysaccharide (referred to as the "collagen-mucopolysaccharide composite layer" hereinafter), and said collagen is crosslinked with a crosslinking agent.

BRIEF DESCRIPTION OF THE DRAWING

The drawing is a cross section of one embodiment of an artificial blood vessel composed of the antithrombogenic and tissue-compatible material according to the present invention.

DETAILED DESCRIPTION OF THE INVENTION

In order to solve the foregoing problems of the prior arts, the present inventors have made extensive investigations, and as a result have noted that polytetrafluoroethylene is excellent in mechanical properties such as elasticity, wet strength, etc. and in compatibility with a living body, and in particular, expanded porous polytetrafluoroethylene renders penetration of the living tissue easy, that collagen has excellent compatibility with a living body, and that mucopolysaccharides are excellent in an antithrombogenic property. It has been found that by providing antithrombogenic materials of the present invention which comprises an expanded polytetrafluoroethylene base having a single or plurality of collagen layer(s) provided on the surface thereof and further provided thereon a collagen-mucopolysaccharide composite layer in which collagen molecules are crosslinked intermolecularly and/or intramolecularly, the problems involved in conventional antithrombogenic materials can be solved, and the present invention has been accomplished.

In the antithrombogenic material of the present invention, as expanded porous polytetrafluoroethylene is used as the base material. This porous polytetrafluoroethylene may be prepared by a method which is basically the same as the one described in Japanese Patent Publication No. 13560/67; and as its shape, sheet-like, tubular, rod-like and the like one may be optionally chosen. In such method, an unsintered polytetrafluoroethylene powder is mixed with a liquid lubricant, and the mixture is extruded, calendered, etc. to mold it into a desired form. While the liquid lubricant is or is not removed from the molded product by extraction, evaporation with heating, etc., the molded product is expanded in at least one axial direction; and then while the expanded product is fixed to prevent heat shrinkage, the expanded product is sintered by heating to a sintering temperature of 327° C. or more to fix the expanded structure to provide a porous polytetrafluoroethylene material having improved strength. The prevention of heat shrinkage as referred to herein includes not only a state in which the shrinkage is fully prevented, but also a state in which the shrinkage is partially allowed.

The resulting porous polytetrafluoroethylene has a microfibrous structure comprising extremely thin fibrils and small nodes interconnected with the fibrils. The diameter and length of the fibrils and the size and number of the nodes can be varied by changing the conditions upon expanding and sintering operations, and thus the pore size and the porosity of the porous polytetrafluoroethylene thus obtained can be freely controlled.

In addition to the method described above, porous polytetrafluoroethylene with increased strength can also be obtained by a method as described in Japanese Patent Application (OPI) No. 178228/84 in which a mixture of unsintered polytetrafluoroethylene and a liquid lubricant is molded, and thereafter three steps of removing the liquid lubricant by evaporation, expanding, and sintering are perfomed simultaneously at an ambient temperature higher than the melting point of polytetrafluoroethylene.

In the antithrombogenic material of the present invention, a single layer or a plurality layers of collagen having excellent compatibility with a living body is firstly provided on the surface of the expanded porous polytetrafluoroethylene base described above. In this case, in order to adhere the collagen layer more firmly onto the surface, the surface of the expanded porous polytetrafluoroethylene base may be previously subjected to a plasma glow discharge treatment, if necessary or desired, to activate the surface. The plasma glow discharge treatment may be effected by cleaning the surface of the expanded porous polytetrafluoroethylene base in a conventional manner, and then uniformly exposing the surface to plasma generated by a plasma glow discharge generating device.

Examples of the method for providing the collagen layer include a method of coating an aqueous collagen solution having a concentration of, e.g., 0.1 to 1 wt % onto the surface of an expanded polytetrafluoroethylene base, a method of impregnating an expanded polytetrafluoroethylene base with the aqueous collagen solution described above, or, in the case of providing the collagen layer onto the inner surface of an expanded polytetrafluoroethylene in a form of a container or tube, a method of injecting and evacuating the aqueous collagen solution into them, etc.

In the present invention, the collagen layer is crosslinked with a crosslinking agent, e.g., a polyvalent aldehyde compound such as glutaraldehyde, dialdehyde starch, etc. In the crosslinking step, for example, the expanded polytetrafluoroethylene base having provided thereon the collagen layer is treated by using a physiological saline solution containing, e.g., 0.05 to 0.25% (v/v) of glutaraldehyde in the similar manner as described for coating collagen.

In the case of laminating the collagen layer in multiple layers, the aforesaid treatment is repeated. It is preferred that collagen used herein be one from that the antigenic groups have been removed so that collagen be excellent in compatibility with a living body. This collagen from which the antigenic groups have been removed can be obtained by defatting, for example, bovine tendons or swine tendons using, e.g., lipase, etc., and then decomposing and removing the antigenic peptides using, e.g., pepsin, etc.

Next, the collagen-mucopolysaccharide composite layer is provided on the thus formed collagen layer The mucopolysaccharide used in the composite layer contains a repeating unit of a disaccharide comprising, for example, an amino sugar and uronic acid or galactose, which may have or may not have a sulfate group therein. Examples of the mucopolysaccharide free from the sulfate group include hyaluronic acid and chondroitin. Examples of the sulfate group-containing mucopolysaccharide include chondroitin sulfates such as chondroitin 4-sulfate, chondroitin 6-sulfate, and dermatan sulfate (chondroitin sulfate B), etc.; heparin, heparin sulfate, and keratan sulfate. These mucopolysaccharides are extremely excellent in an antithrombogenic property and good in compatibility with living body. In the present invention, heparin, hyaluronic acid, and chondroitin sufates are particularly preferably used. These mucopolysaccharides can be used singly or as a mixture thereof.

Examples of the method for providing the collagen-mucopolysaccharide composite layer onto the collagen layer include (1) a method of coating an aqueous mixed solution containing from 0.1 to 1.0 wt % of collagen preferably free from antigenic groups, and from 0.05 to 1.0 wt % of at least one mucopolysaccharide onto the surface of the above provided collagen layer, (2) a method of impregnating an expanded polytetrafluoroethylene base having provided thereon the collagen layer with the above aqueous mixed solution, and (3) in the case of providing on to the surface of the collagen layer provided on the inner surface of the base material in a form of a container or tube, a method of injecting and evacuating the aqueous mixed solution into them. By repeating such an operation, the composite layer may be laminated in multiple layers; or alternatively, two or more aqueous mixed solutions varying the kind of the mucopolysaccharide may be used to form the composite layer in multiple layers.

In the collagen-mucopolysaccharide composite layers thus formed, collagen must be crosslinked with a crosslinking agent, e.g., a polyvalent aldehyde compound such as glutaraldehyde, dialdehyde starch, etc. The crosslinking with the polyvalent aldehyde compound can be carried out in a manner similar to the crosslinking treatment of the collagen layer described above. The antithrombogenic material obtained by such a crosslinking treatment provides excellent durability. The crosslinking of collagen may be performed separately with the respective collagen layer and the composite layer in this order as described above, or alternatively, the crosslinking of collagen may be performed simultaneously all together after laminating the collagen layer and the composite layer thereon. Namely, in any event, it is sufficient that collagen be finally crosslinked. By this crosslinking treatment, collagen is crosslinked intermolecularly and/or intramolecularly. It is thought that generally both intermolecular and intramolecular crosslinking would be present. It is thought that the mucopolysaccharide would be interpositionally present between the crosslinked collagen molecules; this interposition would be in a chemically bound state or simply in a physically dispersed state, in general, both states being included as a mixture thereof. In any case, the crosslinked composite layer takes place a structure in which collagen and the mucopolysaccharide form a harmonious whole.

That is, by such a crosslinking treatment, both the collagen layer and the composite layer are held without being carried by flowing liquid in contact therewith, e.g., flowing in a tube, for example, water, blood, etc. On the contrary, in the case of performing no crosslinking treatment, the components of the layers are carried away, so that the antithrombogenic property, compatibility with a living body, and durability contemplated by the present invention cannot be maintained.

As one embodiment of the present invention, an example of artificial blood vessels prepared from the thus obtained antithrombogenic material of the present invention is described below, with reference to the drawing.

The drawing is an illustrative view of a cross section of the artificial blood vessel comprising an expanded porous polytetrafluoroethylene tube 1 having provided consecutively thereon a collagen layer 2 and a collagen-mucopolysaccharide composite layer 3, with collagen in these layers being crosslinked. When this artificial blood vessel is transplanted, blood is firstly brought into contact with the collagen-mucopolysaccharide composite layer, whereby albumin and the like are absorbed onto the surface of the composite layer to form a stable plasma protein layer. At this stage, thrombus formation is prevented by the mucopolysaccharide in the composite layer. Next, with passage of time, the collagen-mucopolysacccharide composite layer undergoes gradual decomposition in a living body to finally allow exposure of the collagen layer having good compatibility with a living body. It is considered that, at this stage, while the living tissue would grow and the collagen layer is decomposed, stable living tissue layer having almost the same structure as that of the surface layer of a living blood vessel would penetrate into the fibrils of the expanded porous polytetrafluoroethylene, whereby the artificial blood vessel would be organized.

The antithrombogenic material of the present invention possesses an excellent antithrombogenic property and compatibility with a living body as compared to conventional materials; in in vivo experiments utilizing, for example, the aorta or vena cava in the abdomen of rats or rabbits, substantially no thrombus formation is noted, formation of endothelical cells necessary for patency over a long period of time is excellent, a patency rate when transplanted to rats or rabbits is extremely high as compared to conventional artificial blood vessels. Therefore, the survival period is markedly prolonged.

The antithrombogenic material of the present invention is excellent in an antithrombogenic property and compatibility with a living body, and thus, in addition to the application to artificial blood vessels, extremely valuable as materials for a variety of equipments for clinical application used in regions directly contacted with blood, for example, a blood vessel catheter, a tube for artificial kidney, artificial hearts and lung, a blood vessel bypath tube, an artificial heart pumping chamber, etc., by appropriately changing the region of forming the composite layer to a region in contact with blood.

Hereinafter, the present invention is described in more detail but the scope of the present invention is not deemed to be limited thereto.

EXAMPLE 1

A tube having an inner diameter of 2 mm comprising expanded porous polytetrafluoroethylene having a mean fibril length of 60 μm was subjected to a plasma glow discharge treatment.

In order to effectively treat only the inner surface of the tube, the plasma glow discharge treatment was performed using a Pyrex glass reaction tube having an inner diameter larger than the outer diameter of the tube by about 1 mm and a length of 25 mm.

On the other hand, swine skin was treated with pepsin to solubilize. Then, collagen (component precipitated with 2.5M NaCl) was obtained by serial fractionation with sodium chloride. After dissolving thus obtained collagen in a aqueous acetic acid solution (0.2N), dialysis was repeated to water to prepare a 0.4 wt % aqueous collagen solution.

The plasma glow discharge treated tube obtained above was submerged in the aqueous collagen solution at room temperature for an hour, and further submerged in a physiological saline solution containing 0.2% (v/v) of glutaraldehyde to provide a collagen layer crosslinked with glutaraldehyde onto the surface of the tube.

Next, heparin was added to the above obtained aqueous solution to prepare an aqueous solution containing 0.25 wt % of collagen and 0.1 wt % of heparin. The procedure of submerging the tube having provided the collagen layer in this aqueous solution for an hour and then drying were repeated for three times to provide a collagen-heparin composite layer on the collagen layer.

Next, a tube treated as described above was submerged in an aqueous solution of 15 g of dialdehyde starch in 10 liters of water for 30 minutes followed by drying, and then washing with distilled water. Thereafter, the tube was submerged in a 30 wt % aqueous glycerine solution for one hour and then dried to prepare an artificial blood vessel having an inner diameter of 2 mm.

After the thus obtained artificial blood vessel was sterilized at 38° C. for 6 hours using ethylene oxide gas, the in vivo experiments utilizing the aorta and vena cava in the abdomen of rats and rabbits, respectively, were carried out; thrombus which generally generate rapidly were not formed at all for at least 3 hours.

Further, with respect to the survival period of the rats and rabbits, 7 rats out of 7 rats and 3 rabbits out of 5 rabbits were still alive after 2 months, which has been considered to be impossible with conventional artificial blood vessels.

EXAMPLE 2

A tube having an inner diameter of 2 mm comprising expanded porous polytetrafluoroethylene having a mean fibril length of 60 μm was prepared.

On the other hand, calf tendon was defatted with lipase and then a mixture of acetone and ethanol was added thereto to effect complete defatting. Further, the antigenic groups were decomposed and removed by pepsin under acidic condition (pH ca. 2). Then, after the pH was adjusted to 7.4 by using tris hydrochloric buffer, sodium chloride was added to the solution in such an amount that the sodium chloride solution had a concentration of 0.9 mol based on the whole liquid amount, and then centrifugation followed.

The supernatant was collected and sodium chloride was added thereto in such an amount as to provide a 3 mol solution with respect to the concentration of sodium chloride, to thereby precipitate and fractionate atelocollagen. The obtained atelocollagen was solubilized with 0.04N hydrochloric acid to adjust the viscosity to 2,500 cps (measured by a B type viscometer); thus an acid-swelled atelocollagen solution was prepared.

The aforesaid tube was submerged in the acid-swelled atelocollagen solution for 2 hours in vacuum to effect coating the inside of the tube and then dried, which was then repeated. Then, a neutral pH solution containing 0.4 wt % of atelocollagen purified in such a manner as described above and 0.25 wt % of sodium heparin (173 heparin units in 1 mg) was prepared and flowed into the inside of the tube under vacuum, followed by drying.

The tube obtained by the operation described above (tube provided two atelocollagen layers and one atelocollagen-heparin composite layer inside the tube) was submerged in a solution of 3 g of dialdehyde starch in 1 liter of water under negative pressure for 5 minutes to effect crosslinking and dried to provide an artificial blood vessel. The thickness of inner laminate layers was approximately 3.5 μm (by scanning electron microscopy).

After the thus obtained artificial blood vessel was sterilized at 38° C. for 8 hours using ethylene oxide gas, transplantation was performed onto the left aorta in the rabbit cervical region. Further, an artificial blood vessel to which no atelocollagen-heparin composite layer was laminated was transplanted to the right aorta in the rabbit cervical region. The cervical region was opened 4 weeks later, and no thrombus was found in the left aorta. On the other hand, hematostatic thrombus generated in a length of about 4 mm from the anastomotic influx region of the artificial blood vessel comprising atelocollagen containing no heparin.

EXAMPLE 3

A glass rod having an outer diameter of 1.5 mm was inserted into an expanded porous polytetrafluoroethylene tube (length of fibrils: 60 μm in average; inner diameter of the tube: 1.5 mm; length of the tube: 1 cm). Two cycles of coating an acid-swelled atelocollagen solution prepared and purified as in Example 2 onto the outer surface of the tube and then drying were repeated to provide atelocollagen layers laminated in two layers.

The tube was submerged in 0.3% dialdehyde starch solution for 15 minutes to effect crosslinking and then dried. Then, the tube was submerged in distilled water for 30 minutes, and the glass rod was withdrawn from the tube.

Thereafter, the outer surface of the tube was covered with Teflon-made sealing tape so as not to form a coating laminate at the outer surface upon a subsequent treatment of coating the inner surface.

Next, the tube was treated in a manner similar to Example 2, by laminating two atelocollagen layers and one atelocollagen-heparin composite layer in the inside of the tube, crosslinking with 0.3% dialdehyde starch solution for 5 minutes, drying, and then washing with distilled water several times; thus, an artificial blood vessel was formed having the atelocollagen layers at the outer surface, and the atelocollagen layers and the atelocollagen-heparin composite layer thereon at the inner surface.

The thus obtained artificial blood vessel was transplanted to the abdominal aorta of 7 rats (age: 10 months). The abdomen was opened 6 weeks after, and as a result, the formation of good endothelical cell-like cell was confirmed in all cases by observation with the naked eye and by pathohistological survey.

On the other hand, in the case in which a tube comprising expanded porous polytetrafluoroethylene alone (having the same fibril length and the same length and inner diameter of the tube) was transplanted to the abdominal aorta of the another 7 rats (age: 10 months), respectively, and the abdomen was opened 6 weeks after, expansion of endothelium from the anastomotic region was gradually made but endothelium was not produced over the entire surface by pathohistological survey.

EXAMPLE 4

Calf tendon was defatted by lipase, further defatted with a mixture of acetone and ethanol, treated with pepsin to decompose and remove antigenic peptides, and then purified to prepare acid-soluble atelocollagen. The acid-soluble atelocollagen was dissolved in a diluted hydrochloric acid aqueous solution (pH 2.2) to prepare 0.5 wt % acid-swelled atelocollagen solution. Next, a diluted sodium hydroxide aqueous solution was dropwise added to the solution with stirring to homogenize it in a weak alkaline condition.

Then, an aqueous solution of 0.1 g of sodium hyaluronate and 0.2 g of sodium heparin (173 heparin units in 1 mg) in distilled water was added to the solution to adjust the final volume to 200 ml. After the mixture was throughly stirred to be homogeneous, defoaming was performed in vacuum.

An expanded porous polytetrafluoroethylene tube (fibril length: 60 μm in average, inner diameter of the tube: 3 mm, length of the tube: 5 cm) was treated in a manner similar to Example 2 using the thus prepared solution, and an artificial blood vessel was prepared by coating atelocollagen onto the inner surface of the tube twice, drying, a solution of the sodium hyaluronate, heparin sodium, and atelocollagen onto the surface of the atelocollagen layer twice, crosslinking with dialdehyde starch, drying, thoroughly washing with distilled water, drying, and finally sterilizing with ethylene oxide gas.

The artificial blood vessel was transplanted to the cervical aorta of dogs, and as the result, suture was easily done at the anastomotic region with excellent flexibility and elasticity; the cervical region was opened 3 hours after, but no thrombus was formed at all.

EXAMPLE 5

An expanded porous polytetrafluoroethylene tube (fibril length: 60 μm in average, inner diameter of the tube: 2 mm, length of the tube: 2 cm) was submerged in a solution containing 0.4 wt % of neutral region atelocollagen and 0.25 wt % of sodium heparin (173 heparin units in 1 mg) prepared in the same manner as in Example 2, which was allowed to inflow under vacuum in a manner similar to Example 2 followed by drying. The procedure was repeated to coat in three layers. Then, the tube was submerged in a solution of 3 g of dialdehyde starch in 1 liter of water under negative pressure for 5 minutes to effect crosslinking to provide an artific- ial blood vessel. The artificial blood vessel was stained with a basic pigment. Microscopic observation revealed defects of uneven coating, being heterogeneous and being readily stripped off were confirmed. Then, the acid-swelled atelocollagen solution used in Example 2 was flowed into an expanded polytetrafluoroethylene tube having the same properties under vacuum and dried, the procedure was again repeated, the aforesaid mixture of atelocollagen and heparin was coated on the thus obtained tube under vacuum, dried, and crosslinked with a dialdehyde starch solution under the same conditions. This was stained with a basic pigment and microscopically observed; a good quality artificial blood vessel free from either stripping off or uneven coating was obtained.

Thus, it was confirmed that the mixture of atelocollagen and heparin had affinity to a living body-derived protein, but did not have affinity to expanded polytetrafluoroethylene.

While the invention has been described in detail and with reference to specific embodiments thereof, it will be apparent to one skilled in the art that various changes and modifications can be made therein without departing from the spirit and scope thereof.

What is claimed is:

1. An antithrombogenic material consisting essentially of an expanded polytetrafluroethylene base having a collagen layer provided on the surface thereof, and a composite layer of collagen having mucopolysaccharide dispersed therein, provided on said collagen layer, wherein the collagen in said collagen layer and said composite layer is crosslinked with a crosslinking agent.

2. An antithrombogenic material as in claim 1, wherein said crosslinking agent is a polyvalent aldehyde compound.

3. An antithrombogenic material as in claim 2, wherein said polyvalent aldehyde compound is selected from at least one member of the group consisting of glutaraldehyde and dialdehyde starch.

4. An antithrombogenic material as in claim 1, wherein said mucopolysaccharide is selected from the group consisting of heparin, hyaluronic acid, chondroitin sulfate, and a mixture thereof.

* * * * *